United States Patent [19]

Soukup

[11] Patent Number: 5,536,867

[45] Date of Patent: Jul. 16, 1996

[54] PROCESS FOR THE MANUFACTURE OF DICARBOXAMIDES

[75] Inventor: Milan Soukup, Kaiseraugst, Switzerland

[73] Assignee: Hoffmann-La Roche Inc., Nutley, N.J.

[21] Appl. No.: 405,683

[22] Filed: Mar. 17, 1995

[30] Foreign Application Priority Data

Apr. 27, 1994 [EP] European Pat. Off. ............ 94106570

[51] Int. Cl.⁶ ................................. C07C 323/63
[52] U.S. Cl. ........................................ 560/10
[58] Field of Search ................. 560/10; 562/508

[56] References Cited

U.S. PATENT DOCUMENTS 5,399,748  3/1995  Broughton et al. ............ 562/427

FOREIGN PATENT DOCUMENTS 169937  2/1986  European Pat. Off. .

OTHER PUBLICATIONS

Low et al., Bioorganic & Medicinal Chemistry Letters, vol. 2, No. 4, pp. 325–330, @1992.
Chen et al., J. Org. Chem., @1988, 53, 4589–4590.
Bhatt et al. (CA 90:122015n), @1979.
Schon et al. (CA 158837g), @1983.

Primary Examiner—Johann Richter
Assistant Examiner—Laura L. Stockton
Attorney, Agent, or Firm—George M. Gould; William H. Epstein; Bruce A. Pokras

[57] ABSTRACT

The present invention is directed to a process, and novel intermediates used in the manufacture of, dicarboxamides of the formula I

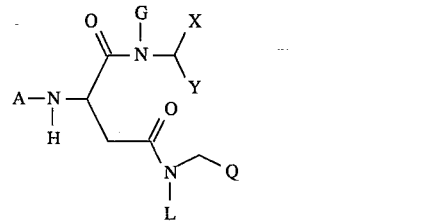

wherein A, G, L, Q, X and Y have the meaning given in the specification, starting from corresponding N-substituted aspartic acid and from corresponding amines G-NHCH(X, Y), via corresponding N-substituted oxazolidinone and N,N-substituted aspartates.

1 Claim, No Drawings

PROCESS FOR THE MANUFACTURE OF DICARBOXAMIDES

SUMMARY OF THE INVENTION

The present invention is concerned with a process for and novel intermediates used in, the manufacture of dicarboxamides of the formula I

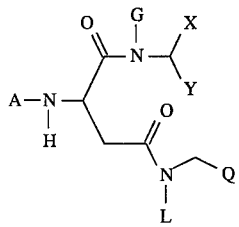

wherein

A is a group $-S(O)_2R^1$, $-S(O)_2N(R^2,R^3)$ or $-C(O)R^4$, $R^1$ is aryl, heteroaryl, heterocyclyl, alkyl or cycloalkyl, $R^2$ and $R^3$ are H, lower-alkyl or aryl-lower alkyl or $R^2$ and $R^3$, together with the N atom, form a group $-N(CH_2)_{4-9}$ optionally interrupted by O or S, $R^4$ is a group $R^{40}$, $-OR^{40}$ or $NHR^{40}$, and $R^{40}$ is lower-alkyl optionally substituted by aryl, heteroaryl or cycloalkyl, or $R^4$ is a lower-alkyl group substituted by lower alkoxycarbonyl, by $-O-$(aryl, heteroaryl or cycloalkyl) or by $-S-$(aryl, heteroaryl or cycloalkyl), G is H, lower-alkyl, lower-alkenyl, aryl, heteroaryl, cycloalkyl, aryl-lower alkyl, heteroaryl-lower alkyl or cycloalkyl-lower alkyl, and X is H, lower-alkyl, aryl, cycloalkyl, aryl-lower alkyl or cycloalkyl-lower alkyl, or G and X, together with the N atom and C atom to which they are bound, form a benzylamino group or a cyclic group $-N(CH_2)_{4-9}$, optionally interrupted by O or S and optionally substituted by up to two substituents of the group of lower-alkyl, $-C(O)O-$lower alkyl and $-CH_2O$-benzyl, Y is H, lower-alkyl or a group $Y^1$ optionally bound via lower-alkylene, $Y^1$ is COOH, COO-lower-alkyl, lower-alkanoyl, lower-alkanoyloxy, lower-alkoxy, aryl-lower alkoxy, $CONH_2$, $CONHOCH_3$, CONHO-benzyl, $CONHSO_2$-lower-alkyl, $CONHCH_2CH_2$-aryl, CONH-cycloalkyl, $CONHCH_2$-heteroaryl, heteroaryl or $C(O)N(CH_2)_{4-9}$ optionally interrupted by O or S and optionally substituted by up to 2 substituents from the group of lower-alkyl, COO-lower-alkyl and $CH_2O$-benzyl, L is H, lower-alkyl or lower-alkoxy-carbonyl-lower alkyl, Q is a group $Q^1$ or $Q^2$:

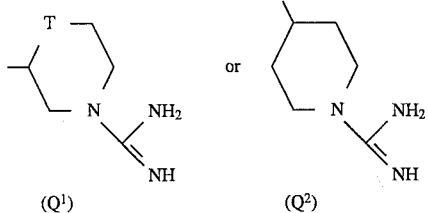

T is $CH_2$ or O.

This process for making the compounds of formula I comprises:

a) reacting aspartic acid with a compound of the formula A-Cl to produce a diacid, of the formula II

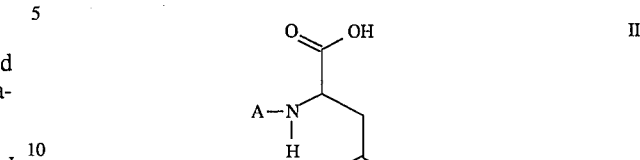

b) reacting the obtained diacid of formula II with formaldehyde to obtain an oxazolidinone of the formula III

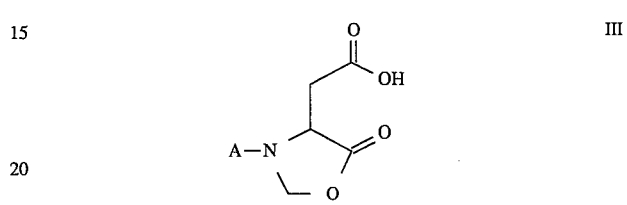

c) reacting the oxazolidone of formula III with an amine of the formula IV

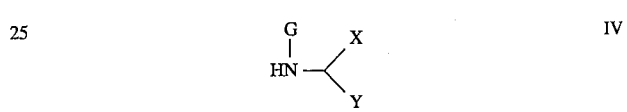

wherein

Y is H, lower-alkyl or a group $Y^1$ optionally bound via lower-alkylene, and

G, X and $Y^1$ are as above, with the restriction that $Y^1$ is not COOH, to yield an acid of the formula V

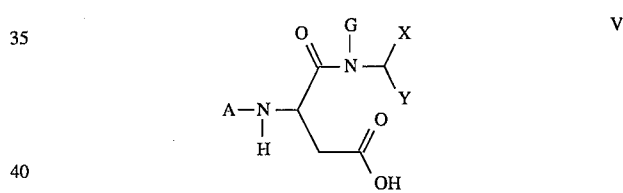

d) reacting the acid of formula V with an amine of the formula $H_2NCH_2-Q$, to produce the dicarboxamide of formula I, and e) where an acid of formula I is desired, wherein Y is a group COOH optionally bound via lower-alkylene, hydrolyzing an obtained lower-alkyl ester of formula I.

DETAILED DESCRIPTION OF THE INVENTION

The present invention is directed to a process for and novel intermediates used in the manufacture of dicarboxamides of the formula I

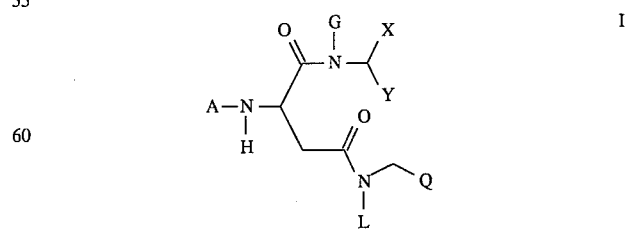

wherein

A is a group $-S(O)_2R^1$, $-S(O)_2N(R^{2,}R^3)$ or $-C(O)R^4$, $R^1$ is aryl, heteroaryl, heterocyclyl, alkyl or cycloalkyl, $R^2$ and $R^3$ are H, lower-alkyl or aryl-lower alkyl or $R^2$ and $R^3$, together with the N atom, form a group $—N(CH_2)_{4-9}$ optionally interrupted by O or S, $R^4$ is a group $R^{40}$, $—OR^{40}$ or $NFIR^{40}$, and $R^{40}$ is lower-alkyl optionally substituted by aryl, heteroaryl or cycloalkyl, or $R^4$ is a lower-alkyl group substituted by lower alkoxycarbonyl, by —O—(aryl, heteroaryl or cycloalkyl) or by —S—(aryl, heteroaryl or cycloalkyl), G is H, lower-alkyl, lower-alkenyl, aryl, heteroaryl, cycloalkyl, aryl-lower alkyl, heteroaryl-lower alkyl or cycloalkyl-lower alkyl, and X is H, lower-alkyl, aryl, cycloalkyl, aryl-lower alkyl or cycloalkyl-lower alkyl, or G and X, together with the N atom and C atom to which they are bound, form a benzylamino group or a cyclic group $—N(CH_2)_{4-9}$, optionally interrupted by O or S and optionally substituted by up to two substituents of the group of lower-alkyl, —C(O)O—lower alkyl and —CH$_2$O—benzyl, Y is H, lower-alkyl or a group $Y^1$ optionally bound via lower-alkylene, $Y^1$ is COOH, COO-lower-alkyl, lower-alkanoyl, lower-alkanoyloxy, lower-alkoxy, aryl-lower alkoxy, CONH$_2$, CONHOCH$_3$, CONHO-benzyl, CONHSO$_2$-lower-alkyl, CONHCH$_2$CH$_2$-aryl, CONH-cycloalkyl, CONHCH$_2$-heteroaryl, heteroaryl or $C(O)N(CH_2)_{4-9}$ optionally interrupted by O or S and optionally substituted by up to 2 substituents from the group of lower-alkyl, COO-lower-alkyl and CH$_2$O-benzyl, $R^a$ and $R^b$ are H, lower-alkyl or phenyl, L is H, lower-alkyl or lower-alkoxy-carbonyl-lower alkyl, Q is a group $Q^1$ or $Q^2$:

T is CH$_2$ or O.

The process for making the compounds of formula I comprises:

a) reacting aspartic acid with a compound of the formula A-Cl to produce a diacid, of the formula II b) reacting the obtained diacid of formula II with formaldehyde to obtain an oxazolidinone of the formula III c) reacting the oxazolidone of formula III with an amine of the formula IV wherein Y is H, lower-alkyl or a group $Y^1$ optionally bound via lower-alkylene, and G, X and $Y^1$ are as above, with the restriction that $Y^1$ is not COOH, to yield an acid of the formula V d) reacting the acid of formula V with an amine of the formula H$_2$NCH$_2$—Q, to produce the dicarboxamide of formula I, and e) where an acid of formula I is desired, wherein Y is a group COOH optionally bound via lower-alkylene, hydrolyzing an obtained lower-alkyl ester of formula I.

Compounds of formula I are known from EP 0 468 231 A3 and EP 0 559 046 A1. They possess valuable pharmacological properties e.g., as thrombin inhibitors, and can be used for the control or prevention of illnesses.

As used in this specification, the term "lower" denotes groups which contain 1 to 6, preferably 1 to 4, C atoms. Thus, lower-alkyl, alone or in combination, denotes straight or branched groups containing 1 to 6, preferably 1 to 4, C atoms such as methyl, ethyl, propyl, isopropyl, butyl, t-butyl, 2-butyl and pentyl.

As used in this Specification, "alkyl", "alkoxy" or "alkenyl" refer to straight or branched chain groups consisting of 1 to 22 C atoms (2–22 C atoms in the case of alkenyl). When $R^1$ is alkyl any alkyl can be used, but the preferred alkyl is a lower-alkyl as enumerated above.

When G is lower-alkenyl, any alkenyl containing 2–6 C atoms can be used. The preferred lower-alkenyl is allyl.

"Aryl" refers to unsubstituted or substituted aromatic groups having 1 or more rings such as phenyl and 1- or 2-naphthyl optionally having one or more substituents such as halogen, e.g. chlorine, or lower-alkyl or alkoxy, e.g. CH$_3$, t-butyl, OCH$_3$, phenyl, CF$_3$, OCF$_3$, cyclopentyl, COOCH$_3$, COOC$_2$H$_5$, CONH$_2$ or tetrazolyl. Where $R^1$ is aryl, the preferred aryl is naphthyl. As used herein, "heteroaryl" groups are 5- to 10-membered aromatic groups which consist of one or 2 rings and which contain one or more N and/or O atoms. Any such heteroaryl may be used. Examples thereof are 2-, 3- or 4-pyridyl, also in the form of their N-oxides, tetrazolyl, oxadiazolyl, pyrazinyl and quinolyl. They can be substituted by any group, e.g. by lower-alkyl such as CH$_3$, or halogen such as chlorine.

"Cycloalkyl" groups refer to saturated hydrocarbon groups forming a ring structure, and contain 3 to 8 C atoms. Any cycloalkyl having 3–8 C atoms can be used. Cyclopropyl, cyclopentyl and cyclohexyl are examples of the preferred cycloalkyl groups.

When G and X together form a cyclic —N(CH$_2$)$_{4-9}$ group, any cyclic-N(CH$_2$)$_{4-9}$ group may be used which is optionally interrupted by O or S and which is optionally substituted by up to two substituents. When the —N(CH$_2$)$_{4-9}$ group is optionally interupted by O, the preferred groups are hexahydroazepino and morpholino.

In the process step a) above, an aqueous solution of aspartic acid, preferably of L-aspartic acid is reacted in the presence of p-toluenesulfonic acid with a sulfochloride or acid chloride of formula A-Cl, conveniently in water and an apolar solvent. Any sulfochloride or acid chloride may be used to produce a diacid of formula II in accordance with this invention. The prefered sulfochloride is 2-naphthalene sulfochloride. When 2-naphthalene sulfochloride is used, there is produced the novel diacid of formula II namely 2-naphthalenesulfonyl-aspartic.

Any organic or inorganic base may be used to carry our the process step a). The preferred base is an alkali metal hydroxide, such as NaOH. Any apolar solvent can be used to produce a diacid of formula II. The preferred solvents are ethylacetate, hexane or toluene. The reaction temperature is not critical, but is preferably a temperature up to 60° C.

The process step b) where the sulfonamide or carboxamide of formula II is cyclized to the oxazolidinone of formula III is conveniently carried out with paraformaldehyde in the presence of an acid, in an aprotic solvent, at a temperature up to reflux, with subsequent H$_2$O separation. Any inorganic or organic acid can be used. The preferred acid is p-toluenesulfonic acid. Any aprotic solvent may be used; however the preferred solvent is toluene.

The process step c) in which an oxazolidone of formula III is reacted with an amine of formula IV can be carried out in an aprotic solvent, such as ethylacetate, at a temperature up to 80° C. While the temperature for this process step c) is not critical, the preferred temperature is 60° C.

The amines IV utilized in the process step c) can be prepared by reacting an amine G-NH$_2$ with a bromide BrCH(X,Y). This is conveniently carried out in the presence of a base, such as triethylamine, in an aprotic solvent, such as hexane at a temperature up to reflux.

The acids of formula V obtained by reacting an oxazolidone of formula IV in accordance with process step c) are novel acids.

The amines H$_2$NCH$_2$—Q utilized in the process step d) can be prepared as described in EP 0 468 231 A3. The amine wherein Q is a N-amidino-piperidinyl group Q$^1$(T=CH$_2$) can also be prepared as follows from 3-picolylamine via 3-aminomethyl-piperidine:

3-Picolylamine can be catalytically hydrogenated, e.g. in water with a rhodium on alumina catalyst in a manner known per se. The obtained 3-aminomethyl-piperidine can be resolved in water and a lower alkanol, such as 2-propanol, with (L)-O,O-dibenzoyltartaric acid. The resulting 3-aminomethyl-piperidine-(L)-O,O-dibenzoyltartarate is then converted into the dihydro-chloride, e.g. by addition of hydrochloric acid. The obtained 3-aminomethyl-piperidine-dihydrochloride can then be reacted with methyl acetoacetate in methanol in the presence of tributylamine in order to selectively protect the primary amino group. The resulting methyl 3-(3-piperidinyl-methylamino)-2-butenoate can then be N-amidinated with 1-amidino-1,2,4-triazolhydrochloride in the presence of tributylamine, in an aprotic or protic solvent, preferably in a lower alkanol, e.g. methanol or ethanol, or in DMF or DMSO, at a temperature up to reflux temperature, preferably at room temperature. The amidinotriazol-salt utilized in the amidination can be prepared by reacting 1,2,4-triazol with cyanamid in the presence of hydrochloric acid in an apolar solvent, such as dioxane.

The amide formation of step d) can be performed using coupling reagents known in the peptide synthesis, especially dicyclohexylcarbodiimide alone or in the presence of catalytic amounts of e.g. N-hydroxysuccinimide.

The optional hydrolysis of step e) can be performed in a protic solvent, with a base. Any protic solvent may be used, such as ethanol. Any inorganic or organic base may be used to carry out this hydrolysis step. The preferred base is an inorganic base, such as NaOH.

The oxazolidones of formula III and the acids of formula V are novel compounds and are an object of this invention. Also an object of this invention is the novel diacid of formula II, namely 2-naphthalenesulfonyl aspartic acid.

EXAMPLE

A) Preparation of the starting materials.

A) 1.a) In a 0.5 l autoclave were added 100 g of 3-picolylamine, 100 ml of water and 5 g of 5%-rhodium on alumina. After degassing and establishing an internal hydrogen pressure of 40 bar, the reaction mixture was heated and stirred for 4 hrs at 50° C. After cooling to rt and flushing with inert atmosphere, the liquid was transferred in a 2 l flask and the autoclave was rinsed with water. The obtained aqueous solution of 3-aminomethyl-piperidine was evaporated under reduced pressure to a weight of 525 g, treated in one portion with 198.8 g (L)-O,O-dibenzoyltartaric acid and cooled to 28° C.

A) 1.b) For crystallization of the resulting (L)-O,O-dibenzoyltartrate, 1 l of 2-propanol was added slowly under stirring. After stirring for 18 hrs, the crystals were filtered and washed with 2-propanol and finally dried under high vacuum at 45° C. The residue was dissolved under stirring at 75° C. in 400 ml of water. This solution was cooled to 28° C. and then treated with 1 l of 2-propanol under stirring over 3 hrs. After stirring overnight at room temperature (rt) the crystals were filtered and washed with 2-propanol and finally dried under high vacuum at 45° C. to yield 193.9 g (44.4%) of the (S)-3-aminomethyl-piperidine-(L)-O,O-dibenzoyltartrate, m.p. 146°–148° C. (dec.), [a]$^{25}_D$=–86.2° (c=1, water).

A) 2) In a 1.5 l flask were added 41.4 g of 1,2,4-triazol, 25.3 g of cyanamid and 600 ml of dioxane. The resulting solution was stirred and heated to reflux. After the addition of 150 ml of 4.15N HCl in dioxane over 1 hr, the reaction mixture was further stirred under reflux for 1.5 hrs. The suspension was cooled slowly to rt and then stirred for 1 hr. The product was filtered, washed with dioxane and dried at 40° C. under high vacuum to yield 85.9 g (97%) of 1-amidino-1,2,4-triazol-hydrochloride, m.p. 198°–199° C.

A) 3.a) In a 2.5 l flask were added 100 g of L-O,O-dibenzoyltartrate product of paragraph A)1.b), 500 ml of water and 1 l of ethylacetate. The reaction mixture was stirred at rt and treated with 80 ml of 25% HCl. After stirring for 15 min, the organic phase was separated and extracted with water. The combined water phases were back extracted with ethylacetate and then evaporated under reduced pressure. The residue was dissolved in a mixture of ethanol and toluene and evaporated again under reduced pressure. To remove the last traces of water this procedure of dissolution and evaporation was repeated to yield 36.6 g (92.4%) of (S)-3-aminomethyl-piperidine-dihydrochloride, [α]$^{25}_D$=−3.6° (c=1, water).

A) 3.b) In a 1.5 1 flask were added 36.6 g of the dihydrochloride of paragraph A)3.a), 300 ml of methanol, 93.3 ml of tributylamine and 23.2 ml of methyl acetoacetate. The suspension was stirred at rt for 5 hrs. As the reaction proceeded, the dihydrochloride dissolved slowly to give a clear solution. After addition of 46.7 ml tributylamine and of 28.9 g of 1-amidino-1,2,4-triazolhydrochloride, the reaction solution was stirred at rt for 18 hrs and then treated at rt over 15 min with 65.2 ml of conc. HCl and subsequently stirred for further 45 min. The reaction mixture was evaporated under reduced pressure. To the residue were added 300 ml of ethanol and the suspension was stirred under reflux for 30 min and at rt overnight. The suspension was cooled to 0° C. and stirred for 2 hrs before filtering the crystals which were washed with ethanol and dried in vacuum at ft. The crude material was suspended in ethanol and the mixture was refluxed and stirred for 30 min, then cooled to rt and stirred for 1 hr. The crystals were filtered, washed with ethanol, dried in vacuum at rt to yield 31.94 g colourless crystals (70%) of (S)-1-amidino- 3-aminomethyl-piperidine-dihydrochloride, m.p. 245°–247° C., [α]$^{25}_D$=−17.4° (c=1, water).

A) 4) To a mixture of 137 ml of cyclopropylamine and 456 ml of triethylamine in 2 l of hexane, were slowly added at rt 180 ml of bromoethylacetate. The resulting suspension was heated under reflux for 2 hrs. After cooling to rt, the precipitate (triethylamine hydrobromide) was filtered, the crystals were washed with hexane and the filtrate was evaporated. The subsequent distillation of the oily residue gave 191.3 g of N-cyclopropyl-ethylglycinate (81%, purity 96% GC).

B) The process.

B) 1) 140 g of (L)-aspartic add and 14 g of p-toluenesulfonic acid were dissolved in 525 ml of 4N NaOH and the solution was cooled to ft. A solution of 227 g of 2-naphthalene sulfochloride in 500 ml of ethylacetate was added dropwise at rt to the reaction mixture. This was warmed to 33°–44° C. and stirred overnight maintaining pH 10 by adding 410 ml of 4N NaOH. After cooling to rt, the phases were separated and the organic phase was washed with 4N NaOH. The combined aqueous phases were washed with ethylacetate, then acidified with 230 ml of conc. HCl to pH 1 and the product was extracted with ethylacetate. The ethylacetate phases were washed with 1/10-sat. NaCl solution, then dried and filtered. The filtrate was evaporated under reduced pressure and the residue dried at 40° C. under high vacuum to 352.7 g of (S)-N-( 2-naphthalenesulfonyl)-aspartic acid as a viscous oil. This material was used directly in the next step. For analytical purposes the crude material was crystallized from methylenechloride, m.p. 94°–96° C., colourless crystals.

B) 2) 330 g of the sulfonamide product of paragraph B)1., 60 g of paraformaldehyde and 10.9 g of p-toluenesulfonic acid were dissolved in 5 l of toluene. The reaction mixture was heated under reflux with water separation, for 80 min. After cooling to rt, the suspension was stirred for 2 hrs, the precipitate was filtered, washed with toluene and with hexane. The product was dried under high vacuum at 40° C. to 287 g (91% from L-aspartic acid) of (R)- 4-carboxymethyl-3-(2-naphthalenesulfonyl)-5-oxazolidinone as colourless crystals, m.p. 143°–144° C. This material was directly used in the next step.

B) 3) 50 g of the oxazolidinone product of paragraph B)2., 107.5 g of N-cyclopropyl-ethylglycinate of paragraph A)4. and 200 ml of ethylacetate were stirred at 60° C. for 7.5 hrs, then cooled to rt and poured into 200 ml sat.-NaHCO$_3$ solution. The two phases were separated and the aqueous phase was extracted with ethylacetate. The combined organic phases were washed with sat.-NaHCO$_3$ solution, dried and then subjected to distillation to recover the excess of N-cyclopropyl-ethylglycinate. The combined aqueous phases were acidified to pH 1 with conc. HCl, stirred for 15 rain and extracted with ethylacetate. The organic phases were washed with sat.-NaCl solution, dried and filtered. The filtrate was evaporated under reduced pressure. The residue was dried under high vacuum at 40° C. to yield 55.8 g of (S)-N-cyclopropyl-N-ethoxy-carbonylmethyl- 3-(2-naphthalenesulfonylamino)-succinamic acid (83%, as a white foam), purity according to HPLC: 96.2%, [α]$^{25}_D$=−26.9° (c=1, methanol). For analytical purposes, the crude product was dissolved in acetone and treated with 1 equiv. of dicyclohexylamine. The resulting dicyclohexylammonium salt was crystallized from ether/hexane, m.p. 142.5°–143.5° C.

B) 4) 54.94 g of (S)-1-amidino-3-aminomethyl-piperidine-dihydrochloride (paragraph A)3.b) were dissolved in 239.8 ml of 1N NaOH solution. To this stirred solution, 102.5 g of the aspartamide product of paragraph B)3., dissolved in 450 ml of tetrahydrofuran (THF), were slowly added. During the addition, the reaction temperature increased to 30° C. and the pH of the solution changed to 7.4. After addition of 2.63 g of N-hydroxysuccinimide and cooling to 14° C. (pH= 6.92), 65.9 g of dicyclohexylcarbodiimide were slowly added (pH=7.3) while maintaining the same temperature. After addition, the reaction mixture was stirred for 1 hr, warmed to rt, and stirring was continued overnight. The precipitated urea was filtered off, washed with aqueous THF, then with THF. The filtrate was diluted with water and extracted with ethylacetate. The combined organic phases were washed with water and discarded. Addition of methylenechloride to the combined water phases resulted in separation into three phases. The two lower phases were separated and the water phase was extracted with methylenechloride. The combined org. phases were evaporated under reduced pressure to give 140.6 g (98% yield) of crude N-[N4-[[(S)-1-amidino-3-piperidinyl]methyl]-N2-( 2-naphthalene-sulfonyl)-L-asparaginyl]-N-cyclopropylglycine ethylester, which was used without purification in the next step. NMR in DMSO-d$_6$:0.82 (m,4H), 1.41 (t,3H), 1.1–1.78 (m, 6H), 2.16 (dxd, 1H), 2.50 (s,1H), 2.50–2.80 (m, 1H), 2.75–2.90 (m,4H), 3.50–4.05 (m,6H), 5.26 (q, 1H), 7.38 (bs,4H), 7.65–8.43 (m,9H).

B) 5) a) To a solution of 140.5 g of the ethylester product of paragraph B) 4 in 700 ml of ethanol, were added in 5 min. at rt 564 ml of 1N NaOH solution. The reaction mixture was stirred at rt for 90 min. After acidification with 1N HCl to pH=7.0, the solution was evaporated under reduced pressure.

B) 5) b) The product of paragraph B)5.a) was suspended under reflux in 2 l of ethanol and 10 ml of water. The suspension was heated and the solid precipitate (NaCl) filtered and washed with ethanol. The filtrate was evaporated under reduced pressure. The crude product was dissolved in 1.4 l ethanol, the solution was stirred under reflux and then slowly cooled to rt. To this suspension 1 l of ethylacetate was added. The suspension was stirred for 2 hrs, the resulting crystals were filtered, washed with ethylacetate and finally dried at 40° C. under vacuum and then at rt under high vacuum to yield 109.7 g of N-[N4-[[(S)-1-amidino-3-piperidinyl]methyl]-N2-(2-naphthalenesulfonyl)-L-asparaginyl]-N-cyclopropylglycine (purity 88.6% HPLC).

B) 5) c) 108.7 g of the product of paragraph B)5.b) were suspended in 3 l of ethanol and 42 ml of water. The slurry was stirred under reflux for 30 min, and hot filtered. The filter was washed with ethanol and the filtrate was cooled to rt and stirred overnight. The crystals were filtered, washed with ethanol and dried at 40° C. under high vacuum to 72.5 g colourless crystals of purity: 8.7%, HPLC; m.p. 220°–221° C.

B) 5) d) The mother liquor was evaporated under vacuum. The residue was suspended in 500 ml of ethanol and 8 ml of water and the suspension was refluxed for 30 min. After filtration of the hot solution and washing with ethanol, the filtrate was cooled to rt and stirred for 16 hrs. The precipitate was filtered and washed with ethanol. The crystals were dried at 40° C. under high vacuum to 14.9 g colourless crystals of purity: 94.8% HPLC, m.p. 220°–223° C.

B) 5) e) The evaporation residues from mother liquors from paragraph B)5.b) and B)5.d) were combined and dissolved in 90 ml of ethanol and 10 ml of water. The solution was filtered through silica gel. After elution with 90 vol.-% of aqueous ethanol, the fractions 3–5 were combined and evaporated at 40° C. under reduced pressure. The residue was dissolved in boiling ethanol. The hot turbid solution was filtered, cooled to rt and stirred overnight. The precipitate was filtered, washed with ethanol and dried at 40° C. under high vacuum. The product was recrystallized from boiling 200 ml of ethanol and 3 ml of water to 4.27 g product (purity: 99% HPLC), m.p. 220°–223° C.

I claim:

1. The compound (S)-N-cyclopropyl-N-ethoxycarbonyl-methyl-3-(2-naphthalenesulfonylamino)-succinamic acid.

\* \* \* \* \*